United States Patent [19]

Shaposka et al.

[11] Patent Number: 4,770,735

[45] Date of Patent: Sep. 13, 1988

[54] TECHNIQUES FOR WELDING THERMOPLASTIC TUBES

[75] Inventors: John B. Shaposka; Dudley W. C. Spencer, both of Wilmington, Del.

[73] Assignee: Denco, Inc., Del.

[21] Appl. No.: 99,714

[22] Filed: Sep. 22, 1987

[51] Int. Cl.[4] .................. B29C 65/18; F16L 41/02; F16L 47/02

[52] U.S. Cl. ................... 156/258; 156/304.2; 156/304.5; 156/304.6; 156/503; 285/156; 604/905

[58] Field of Search ............ 156/159, 158, 258, 296, 156/304.2, 304.5, 304.6, 502, 503, 510; 604/905; 285/156

[56] References Cited

U.S. PATENT DOCUMENTS

| | | | |
|---|---|---|---|
| 3,116,756 | 1/1964 | Alderson | 285/156 |
| 3,873,391 | 3/1975 | Plauka et al. | 156/258 |
| 4,240,855 | 12/1980 | Pennington | 156/304.6 |
| 4,369,779 | 1/1983 | Spencer | 156/159 |
| 4,641,860 | 2/1987 | McMickle et al. | 285/156 |

Primary Examiner—Michael Wityshyn
Attorney, Agent, or Firm—Connolly & Hutz

[57] ABSTRACT

Thermoplastic tubes are welded together in a dry condition with the tubes being open and maintained in their undistorted condition during the welding step. In an alternative technique a branch tube is welded to a main tube by placing the tubes in a non-parallel orientation in a holding device. A wafer cuts completely through one tube to form two tube sections. The wafer also cuts a notch from the other tube. One of the tube sections is shifted to become aligned with the notched other tube and welded thereto. A further technique includes placing at least one tube in a holding device which has a false floor for pressing against an area of the tube while the tube is being flattened at two spaced locations on opposite sides of the area. When the false floor is moved away from the tube a partial vacuum results. An air pocket is formed when the tube is severed by a wafer by air flowing into the cut tube.

16 Claims, 3 Drawing Sheets

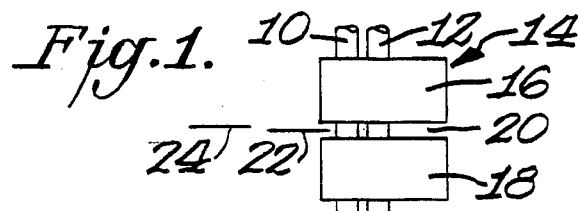
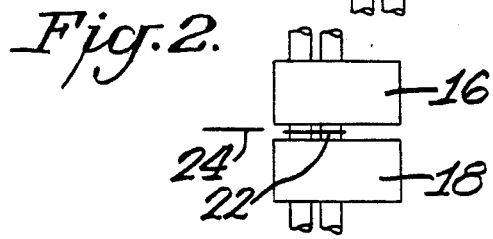
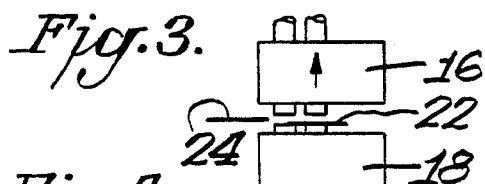
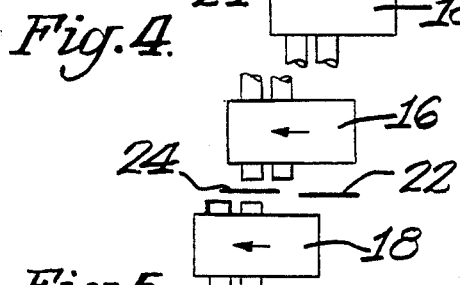
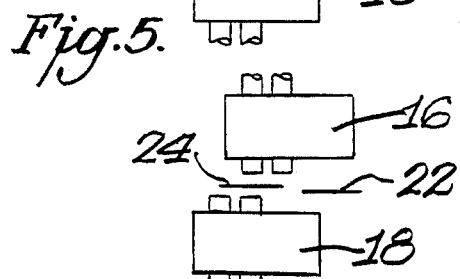
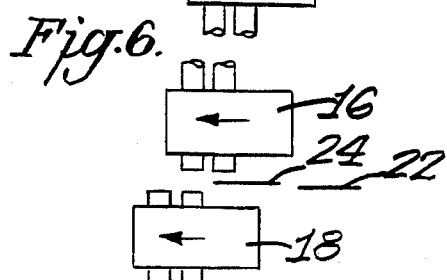
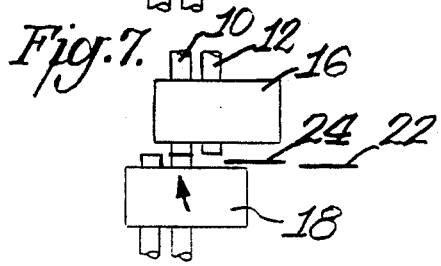
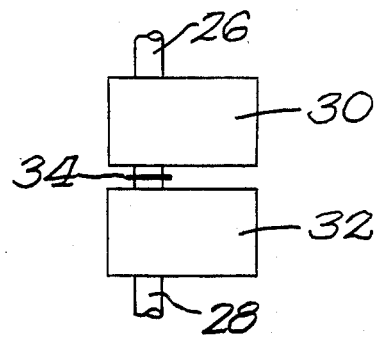
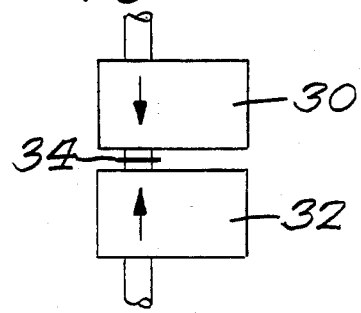
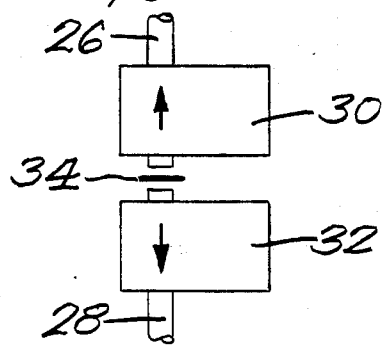
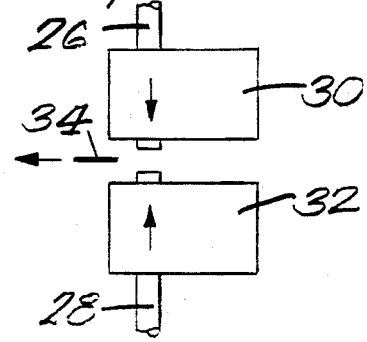

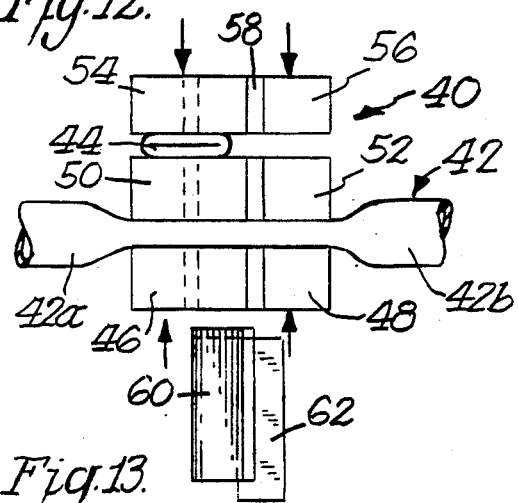
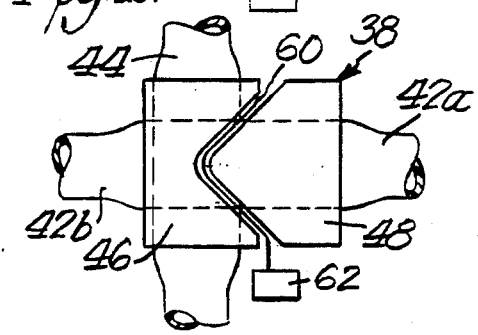
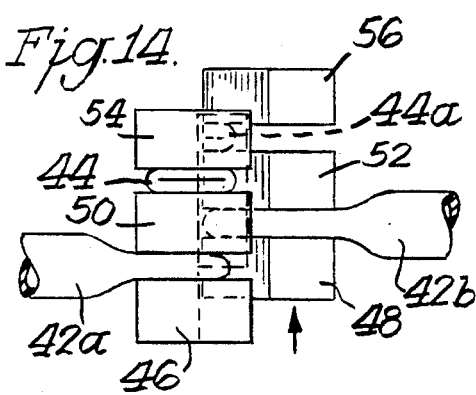
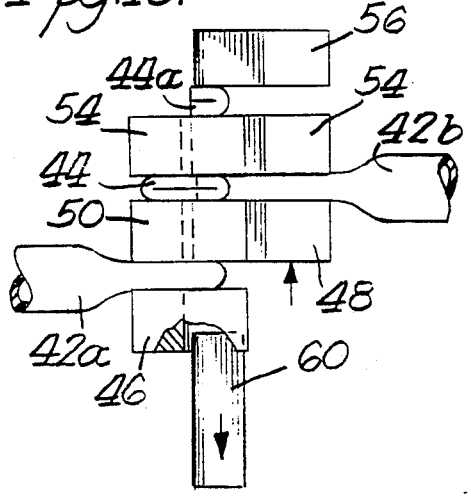
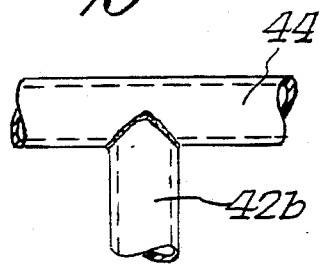
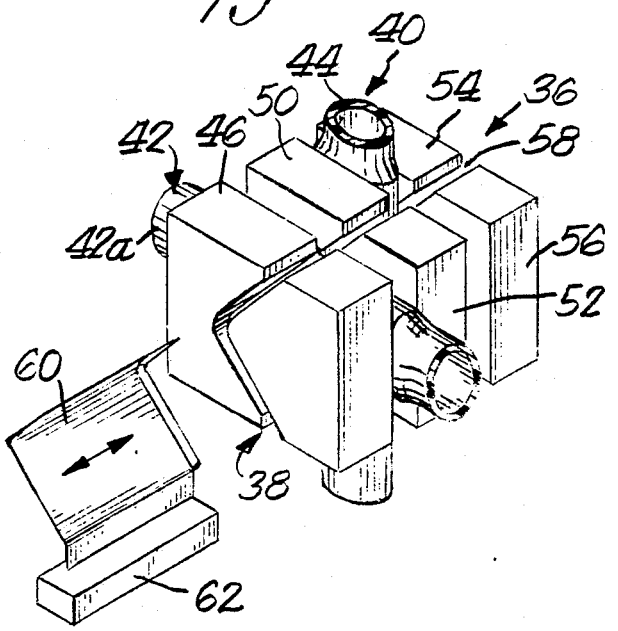

TECHNIQUES FOR WELDING THERMOPLASTIC TUBES

BACKGROUND OF INVENTION

This invention relates to improvements in the welding of thermoplastic tubes. Various techniques are known for such welding operations. Copending application Ser. No. 51,390, filed May 18, 1987, the details of which are incorporated herein by reference thereto, discusses prior techniques as well as the particular techniques which are the subject of that invention. A common use of such techniques is in dialysis when it is necessary to provide a patient with a fresh supply of liquid dialysate. Under such circumstances the tube containing the old dialysate which leads from the patient to the supply is severed. The same apparatus severs a tube leading from the new supply. The conventional techniques involve realigning the cut tubes so that the tube section from the new supply becomes aligned with the tube section from the patient. These aligned tube sections are then welded together to provide the patient with fresh dialysate.

The main emphasis in the techniques used heretofore have been concerned with the welding of fluid-filled tubes. With such techniques means had to be provided to flatten or seal each tube at two spaced locations so that a cutting device, usually a heated wafer, may cut through the tube between the two spaced locations.

The conventional approaches taken heretofore have also been generally confined to cutting through parallel tubes and then realigning the tube so as to form a single welded tube. Under certain circumstances, however, it would be desirable if the techniques could be utilized for welding a branch tube to a main tube.

It would also be desirable if techniques could be provided which are capable of welding fluid filled tubes wherein the cutting and welding steps take place in a portion of the tubes where there is no fluid.

SUMMARY OF INVENTION

An object of this invention is to provide a method of welding thermoplastic tubes which are severed and welded while in their dry undistorted condition.

A further object of this invention is to provide a device and method of welding a branch tube to a main tube.

A still further object of this invention is to provide a device and method for welding round tubes containing fluid wherein the severing and welding steps take place at a location having an air pocket.

In accordance with one aspect of this invention a pair of dry round tubes are mounted in a holding device and are maintained in their dry round condition while the welding step takes place. In one embodiment of this invention, the tubes are mounted in a parallel relation during the severing step and then realigned for the welding step. In an alternative embodiment the tubes are pre-cut and then aligned to eliminate the need for a shifting or realignment step.

A further aspect of this invention involves the welding of a branch tube to a main tube. This is accomplished in a device wherein two tubes are mounted in non-parallel relation with a cutting device, preferably a heated wafer, moving relative to the tubes so as to completely cut through one tube and form two sections and to cut a notch from the other tube. The wafer is preferably non-linear so that non-linear cuts result of complementary shape. The cut tubes are shifted to align one tube section with the complementary shaped notched other tube and these aligned tubes are welded together so that the tube section forms a branch of the other tube.

In yet another practice of this invention the tubes are mounted in a holding device wherein at least one of the holding devices includes two spaced pairs of clamping jaws with a gap therebetween for sealing the tube at two spaced locations. One of the pairs of clamping jaws includes a false floor for pressing against an area of the tube in a compression zone between the spaced locations and forming a partial vacuum in the compression zone. The movement of the false floor away from the tube creates an air pocket at the gap so that a cutting device may cut through the tube at the air pocket.

THE DRAWINGS

FIGS. 1–7 are plan views schematically illustrating the sequence of steps in accordance with one practice of this invention;

FIGS. 8–11 are plan views schematically illustrating the sequence of steps in accordance with a further practice of this invention;

FIGS. 12 is a plan view schematically illustrating the first in a sequence of steps in accordance with yet another practice of this invention;

FIG. 13 is a side elevation view showing a further step in accordance with the practice of FIG. 12;

FIGS. 14–15 are plan views of yet further steps in accordance with the practice of FIGS. 12–13;

FIG. 16 is an elevation view partly in section illustrating the correction of a branch tube to a main tube which results from the practice of the invention illustrated in FIGS. 12–15;

FIG. 17 is a perspective view illustrating the device used in the practice of the invention illustrated in FIGS. 12–15.

DETAILED DESCRIPTION

Figure 18:
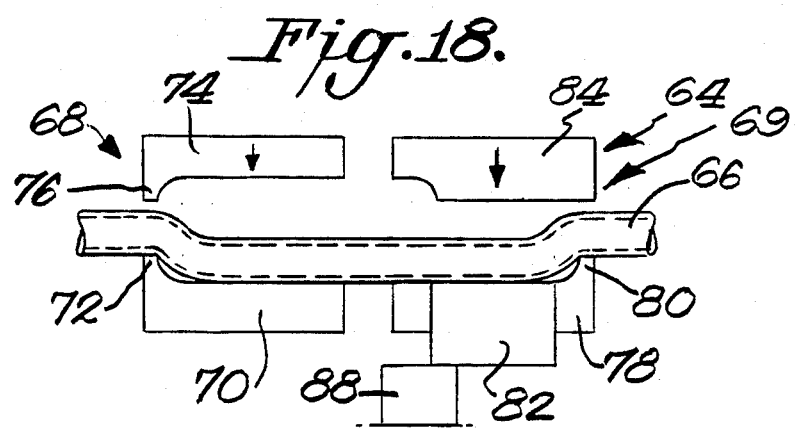
FIGS. 18–21 are elevation views schematically illustrating the sequence of steps in yet still another practice of this invention.
Figure 19:
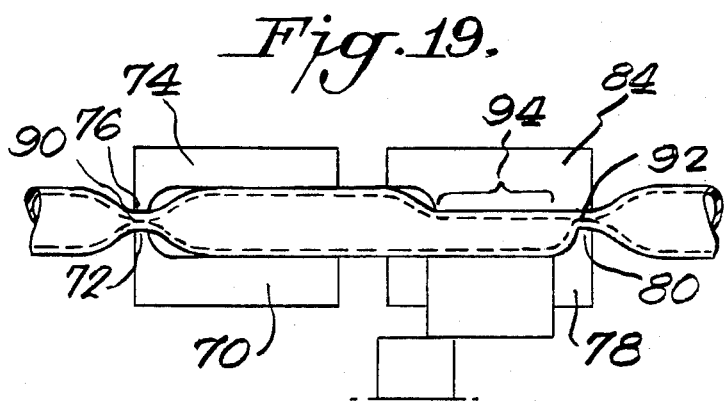

FIGS. 1–7 illustrate a practice of this invention which is remarkably simpler than the conventional practice dealing with the welding of fluid filled tubes since the practice of FIGS. 1–7 is directed to dry tubes. As previously indicated the prior art has concentrated its efforts on the welding of fluid filled thermoplastic tubes such as used in dialysis. There are, however, many circumstances ignored by the prior art where it is desirable to weld thermoplastic tubes which do not contain fluid, but rather are in a dry condition. Such circumstances could include laboratory or test work as well as hospital pharmacy routines or methods wherein fluid is supplied only periodically. FIGS. 1–7 schematically illustrate the principles upon which this aspect of the invention is based. It is to be understood that once given the teachings of this invention those skilled in the art could use any suitable equipment for carrying out the invention. Copending application Ser. No. 51,390 filed May 18, 1987 for example describes suitable equipment which could be modified to eliminate the clamping steps and otherwise be used in the practice of this invention. Accordingly, the details of that application are incorporated herein by reference thereto, rather than describing those details except as is necessary herein for an understanding of this invention.

As shown in FIG. 1 a pair of tubes 10, 12 made of thermoplastic material such as conventionally known in the prior art is mounted in parallel relation in a holding device 14 which includes a first clamp unit 16 and a second clamp unit 18 spaced from each other to form a gap 20. Although units 16 and 18 are referred to as clamp units, the only clamping that is necessary is to hold the tubes in place without flattening the tubes which differs from the prior art approach. During this loading step wafers 22, 24 are heated to their intended temperatures. Wafer 22 is a cutting wafer and is heated for example to 350° F. Wafer 22 is preferably provided with a non-stick surface. Wafer 24 is made for example of nichrome and is heated to a temperature between 500°-1200° F. since it functions in the welding step. Such wafers are known in the art.

FIG. 2 illustrates the severing step in which there is relative movement between the holding device 14 and wafer 22 so that warm wafer 22 passes into gap 20 to cut through tubes 10, 12.

FIG. 3 shows the sequence of operation wherein clamping unit 16 is moved away from clamping unit 18.

FIG. 4 illustrates the realigning step wherein clamping unit 16 is shifted as indicated so that a tube section from tube 10 in clamping unit 16 becomes aligned with a tube section from clamping unit 18. In this step warm wafer 22 is no longer between the cut tubes; rather hot wafer 24 is located between the aligned tube sections.

FIG. 5 illustrates the step wherein there is a pause to allow radiant heat from hot wafer 24 to melt and simultaneously sterilize the aligned tube ends.

FIG. 6 illustrates the step wherein hot wafer 22 is moved away from the aligned tube ends.

FIG. 7 illustrates the final sequence wherein clamping unit 18 is shifted to push the heated aligned tube ends together and effect the weld.

The advantages of the method of FIGS. 1-7 is that it provides a simplified technique for joining round dry tubes.

FIGS. 8-11 show a variation of the method of FIGS. 1-7. As indicated therein tube 26 and tube 28 are pre-cut so that their tube ends are reasonably squared. FIG. 8 illustrates the initial step where the pre-cut tubes 26, 28 are mounted in a pair of clamping units 30, 32 similar to units 16, 18 except that units 30, 32 need accommodate only one tube rather than a pair of tubes. As shown in FIG. 8 tube ends 26, 28 are pressed against a cold wafer 34.

FIG. 9 illustrates the next step of operation wherein the wafer 34 is turned on or heated and the tube ends 26, 28 are pressed into contact with wafer 34 by the shifting of clamping units 30, 32. During this step the surface of the tube ends is flattened to assure proper contact during the later welding step. The presence of the non-heated tubes holds down the wafer temperature. The wafer itself could be provided with a built-in temperature control.

FIG. 10 illustrates the next step wherein clamping units 30, 32 are moved away from each other to pull the tubes out of contact with and away from wafer 34. This allows the wafer temperature to rise and radiantly melt the exposed tube ends.

FIG. 11 shows the next step wherein wafer 34 is moved away from the tube ends. Clamping units 30, 32 are then moved toward each other to press the tube together and make the weld.

The practice of FIGS. 8-11 thus includes all of the advantages of the practice of FIGS. 1-7 but is even more simplified because it eliminates the shifting step.

FIGS. 12-17 relate to the practice of this invention wherein a branch tube is connected to a main tube. The device for practicing this embodiment of the invention is best illustrated in FIG. 17. It is noted that this practice may be used with fluid filled tubes.

As shown in FIG. 17 branch welding device 36 includes a holding device which comprises a first pair of clamping units 38 and a second pair of clamping units 40. Clamping units 38 clamps a first tube 42 in a particular orientation while clamping unit 40 clamps a second tube 44 in a non-parallel orientation. For example, as illustrated one of the tubes 42 is horizontal while the other tube 44 is vertical or perpendicular thereto. It is to be understood however that any suitable non-parallel relationship may be used within the practice of this invention. Each clamping unit comprises two sets of clamping jaws. Clamping unit 38 includes for example a set of clamping jaws 46, 48 and a second set of spaced clamping jaws 50, 52 so as to press against and clamp tube 42. Clamping unit 40 includes a pair of clamping jaws 54, 56 which cooperate with clamping jaws 50, 52 to clamp tube 44. The various clamping jaws are spaced from each other to provides gaps which jointly form an unobstructed path 58 into which the tubes 42 and 44 extend.

In the preferred practice of this invention the cutting and heating is accomplished by a wafer 60 which is bent so as to be non-linear. Wafer 60 is positioned for relative movement in path 58 by either maintaining the wafer stationery and moving holding device 36 or, as illustrated, by mounting wafer 60 on any suitable support 62 which would be appropriately positioned so that it could move wafer 60 through path 58 without support 62 contacting the tubes.

FIG. 12 shows the step wherein tubes 42, 44 are mounted in the clamping units 36, 40 and flattened by moving clamping jaws 46, 48 and jaws 54, 56 toward stationary jaws or anvils 50, 52 as indicated by the arrows.

After the flattening step of FIG. 12 the severing step of FIG. 13 takes place. As illustrated wafer 60 cuts completely through tube 42 to form a pair of tube sections 42a, 42b. Because wafer 60 is non-linear the tube sections likewise have non-linear ends. As wafer 60 continues to move through path 58 wafer 60 cuts a notch from tube 44 with the notch having a shape complementary to the non-linear end of tube end 42b such as a V-shape. The severed material 44a (FIGS. 14-15) would have a shape complementary to tube end 42a. As illustrated, path 58 has a shape conforming to the shape of wafer 60.

FIG. 14 illustrated the next step of operation wherein wafer 60 is removed from path 58 and the clamping jaws are moved toward the realigning position that is illustrated in FIG. 15. In this realigning position tube end 42b fits into the notch in tube 44. Tube end 42 comprises a stub end which is sealed because of its flattened condition. Several material 44a will later be discarded. The aligned tube end 42b and tube 44 are then pressed together as shown in FIG. 15 to effect the welding operation in the known manner.

FIG. 16 illustrates the resulting tube structure wherein tube 44 comprises a main tube and tube end 42b is the branch tube.

The embodiment of FIGS. 12-17 has a number of advantages. For example, the tubes 42, 44 need not be of the same diameter to be joined together. Additionally, the branch tube could be connected to the main tube at any angle and need not be perpendicular thereto.

FIGS. 18-21 illustrate yet a further practice. The device 64 is utilized for forming an air pocket in the tube being cut so that the wafer may cut through the air pocket in the otherwise fluid filled tube. FIGS. 18-21 illustrate the practice of this invention involving the cutting of a single tube. The invention may be practiced wherein the same concept of air pocket cutting may be used for both tubes to be welded together or wherein an air pocket is formed in only one of the pair of tubes.

As shown in FIG. 18 tube 66 is loaded or installed in spaced holding devices 68, 69 having a gap therebetween. Each holding device comprises a set of clamping jaws. One set of clamping jaws includes a lower jaw 70 having a clamping edge 72. Jaw 70 is associated with upper jaw 74 having a clamping edge 76. The second set of clamping jaws includes a lower jaw 78 having a clamping edge 80. The central portion of clamping jaw 78 includes a passageway which is plugged by a false floor 82 in the form of a slidable block having its upper surface generally coplanar with the upper surface of jaw 78 as illustrated. Upper clamping jaw 84 has a flat lower surface 86 along the major part of its length so that a corner of clamping jaw 84 is located in line with clamping edge 80. A trigger 88 or movable stop is located below false floor 82 to maintain false floor 82 in the position shown in FIG. 18.

When upper clamping jaws 74 and 84 are moved downwardly toward the lower clamping jaws tube 66 is sealed or flattened at two spaced locations 90, 92. An area of tube 66 is also compressed where clamping jaw 84 presses the tube 66 against false floor 82. This area is referred to as a compression zone 94. The portions of tube 66 outwardly of sealed points 90, 92 is under normal pressure. In the condition shown in FIG. 19 tube 66 is filled with fluid throughout the region between sealed points 90, 92.

Figure 20:
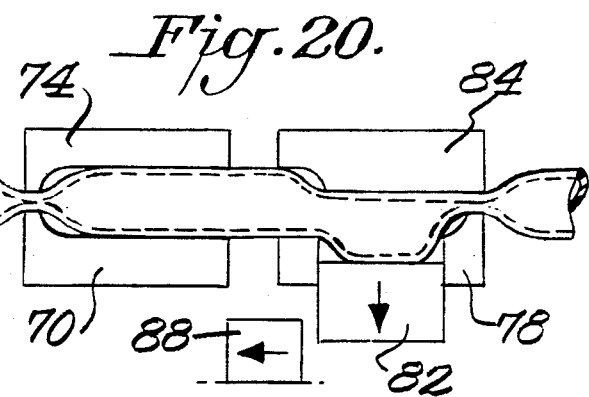

FIG. 20 shows the next step of operation wherein trigger 88 is shifted out of contact with false floor 82. As a result floor 82 drops in the passageway of clamping jaw 78 so that tube 66 is no longer under compression in the compression zone. As a result tube 66 tends to expand toward its original diameter which creates a partial vacuum in compression zone 94. At the same time the wafer holder is beginning to move wafer 96 into the gap 98 between the clamping units 64, 68.

Hot wafer 96 is then moved through gap 98 to cut through tube 66. The severing of tube 66 by the hot wafer 96 creates an air pocket 100 to be formed caused by air being sucked into the tube 66 as indicated by the arrows 102. The fluid remains in tube 66 without flowing into the air pocket 100 because for example of surface tension with a miniscus being formed at each of the cut ends of tube 66.

Figure 21:
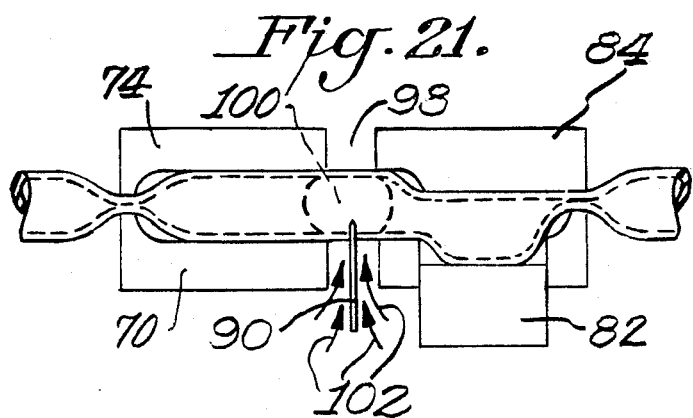

The practice of this invention is particularly intended to be used with small diameter tubes such as ⅜" or less so that the air pocket 100 will be maintained without fluid flowing into the air pocket. It is also to be understood that although FIG. 21 illustrates the cutting operation to take place by using a vertically moving wafer 96, the invention may be practiced with a horizontally moving wafer.

The embodiment of FIGS. 18-21 is particularly advantageous because it utilizes the partial vacuum effect to cause fluid to jump away from the initial cut tube and permit an air pocket to result. Although the cut tube is essentially filled with fluid the presence of the air pocket and the negative pressure products the operator from the contents of the fluid. This practice is also advantageous because it is a simple operation which is transparent to the operator.

After a pair of tubes have been cut, using the concepts of FIGS. 18-21 for at least one tube, the cut tubes are shifted into realignment and welded as previously described.

We claim:

1. A device for forming a branch connection of a thermoplastic tube to the side wall of a second thermoplastic tube comprising a holding device, said holding device comprising a first pair of clamping units for clamping a first tube extending across said clamping units, said clamping units being spaced from each other to provide an unobstructed path therebetween, a second pair of clamping units for clamping a second tube in an orientation non-parallel to the first tube, said second pair of clamping units being spaced from each other and having an unobstructed path in line with and communicating with said unobstructed path of said first pair of clamping units whereby the second tube may extend across said unobstructed path, cutting means relatively movable in said unobstructed path for cutting through the first tube to create a pair of tube sections and for cutting a notch from the second tube, one of said first pair of clamping units and one of said second pair of clamping units on the same side of said unobstructed path being shiftably mounted to realign the cut tubes for aligning one of the tube sections with the second tube at the location of the cut notch, means for heating the notch of the realigned second tube and the cut end of the tube section realigned with the notch, and means for pressing the heated realigned cut tubes to weld the cut tubes together whereby the welded tube section forms a branch to the second tube.

2. The device of claim 1 wherein said cutting means comprises a bent wafer to form non-linear complementary cuts.

3. The device of claim 2 wherein said wafer is heated to comprise said heating means.

4. The device of claim 3 wherein said unobstructed path has a shape conforming to the shape of said bent wafer.

5. The device of claim 4 wherein said first pair of clamping units comprises a first pair of spaced clamping jaws with a portion of said unobstructed path therebetween, a pair of spaced anvils associated with first pair of clamping jaws for inserting the first tube between said first pair of clamping jaws and said pair of anvils, a portion of said unobstructed path being the spacing between said anvils, said second pair of clamping units comprising a second pair of clamping jaws with a portion of said unobstructed path therebetween, and said second pair of clamping jaws being associated with said pair of anvils for inserting the second tube between said second pair of clamping jaws and said pair of anvils.

6. The device of claim 5 wherein said first pair of clamping jaws and said second pair of clamping jaws are movable toward said anvils to flatten the first and second tubes.

7. The device of claim 6 wherein one of said first pair of clamping jaws and one of said anvils and one of said second pair of clamping jaws on the same side of said unobstructed path are laterally shiftable with respect to said clamping jaws and said anvil on the other side of said path to effect the realignment of the tubes.

8. The device of claim 7 wherein said second pair of clamping jaws holds the second tube in an orientation perpendicular to the first tube.

9. The device of claim 2 wherein said wafer has a V-shape.

10. The device of claim 2 wherein said wafer is mounted on a mount for movement into and out of said unobstructed path.

11. The device of claim 2 wherein said wafer is stationarily mounted and said unobstructed path is movable with respect to said wafer.

12. A method for forming a branch connection from a first thermoplastic tube to the side wall of a second thermoplastic tube comprising mounting the first tube across a gap between a first pair clamping units, mounting a second tube in a second pair of spaced clamping units with a spacing between the second pair of clamping units being in line with the gap and forming a continuous unobstructed path and with the second tube being in an orientation non-parallel to the first tube and with the second tube extending across the unobstructed path, moving a cutting device through the unobstructed path to cut the first tube into a pair of cut sections and to cut a notch from the second tube, realigning the tubes to align one of the cut sections with the notched second tube, heating the notch of the realigned second tube and the cut end of the tube section realigned with the notch, and pressing the heated realigned tubes to weld the cut section to the notched second tube whereby the cut section forms a branch of the second tube.

13. The method of claim 12 wherein the cutting device is a bent heated wafer which cuts and heats the tubes.

14. The method of claim 12 wherein the second tube is perpendicular to the first tube.

15. The method of claim 12 wherein the first tube has a different diameter than the second tube.

16. The method of claim 12 wherein the tubes are flattened before being cut.

* * * * *